(12) United States Patent
Maity et al.

(10) Patent No.: US 11,286,240 B2
(45) Date of Patent: Mar. 29, 2022

(54) CATALYST BOUND ALPHA RADICAL AND SYNTHESIS OF OXO COMPOUNDS USING THE SAME

(71) Applicant: Council of Scientific and Industrial Research, New Delhi (IN)

(72) Inventors: Pradip Maity, Maharashtra (IN); Abdul Motaleb, Maharashtra (IN); Asish Bera, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 117 days.

(21) Appl. No.: 16/492,733

(22) PCT Filed: Mar. 9, 2018

(86) PCT No.: PCT/IN2018/050135
§ 371 (c)(1),
(2) Date: Sep. 10, 2019

(87) PCT Pub. No.: WO2018/163217
PCT Pub. Date: Sep. 13, 2018

(65) Prior Publication Data
US 2021/0147364 A1    May 20, 2021

(30) Foreign Application Priority Data
Mar. 10, 2017  (IN) .............. 201711008390

(51) Int. Cl.
| | | |
|---|---|---|
| *C07D 219/02* | (2006.01) | |
| *B01J 31/02* | (2006.01) | |
| *C07D 215/227* | (2006.01) | |
| *C07D 217/24* | (2006.01) | |

(52) U.S. Cl.
CPC ........ *C07D 219/02* (2013.01); *B01J 31/0285* (2013.01); *B01J 31/0298* (2013.01); *C07D 215/227* (2013.01); *C07D 217/24* (2013.01); *B01J 2231/70* (2013.01); *B01J 2531/002* (2013.01)

(58) Field of Classification Search
CPC .............. C07D 219/02; C07D 215/227; C07D 217/24; B01J 31/0285; B01J 31/0298; B01J 2231/70; B01J 2531/002
See application file for complete search history.

(56) References Cited

PUBLICATIONS

Chen; Chem. Asian J. 2010, 5, 328-333. (Year: 2010).*
Grignon-Dubois; Syn. Commun., 1995, 25, 2999-3006. (Year: 1995).*
Jin; J. Am. Chem. Soc. 2017, 139, 14237-14243. (Year: 2017).*
Motaleb; Org. Biomol. Chem., 2018, 16, 5081-5085. (Year: 2018).*
Paira; Tetrahedron 2008, 64, 4026-4036. (Year: 2008).*
Reddy; Syn. Commun., 2001, 31, 3447-3451. (Year: 2001).*
Seo; J. Org. Chem. 2015, 80, 24, 11993-11998. (Year: 2015).*
Singh; Synthesis 1983, 791-793. (Year: 1983).*
Wang; Green Chem., 2018, 20, 3302-3307. (Year: 2018).*
Zhou; Org. Chem. Front., 2020, 7, 2405-2413. (Year: 2020).*
Leow; Org. Lett. 2014, 16, 21, 5812-5815. (Year: 2014).*
Demidov; Chemistry of Heterocyclic Compounds, 2009, 45(5), 619-620. DOI:10.1007/s10593-009-0309-4 (Year: 2009).*
Ha Seo et al., "Formation of Amides from Imines via Cyanide-Mediated Metal-Free Aerobic Oxidation", The Journal of Organic Chemistry 80(24): 11993-11998 (2015).
D Leow et al., "Phenazinium Salt-Catalyzed Aerobic Oxidative Amidation of Aromatic Aldehydes", Organic Letters 16 (21): 5812-5815 (2014).

* cited by examiner

*Primary Examiner* — Daniel R Carcanague
(74) *Attorney, Agent, or Firm* — Merchant & Gould P.C.; Daniel R. Evans (57) ABSTRACT

The present invention discloses in situ generated catalyst bound alpha radical compound represented by formula (I) or (II) and a single pot process for the preparation of oxo compounds by using in situ generated catalyst bound alpha radical compound of formula (I) or (II).

9 Claims, 1 Drawing Sheet

CATALYST BOUND ALPHA RADICAL AND SYNTHESIS OF OXO COMPOUNDS USING THE SAME

This application is a National Stage application of PCT/IN2018/050135, filed Mar. 9, 2018, which claims priority to Indian Patent Application No. 201711008390, filed Mar. 10, 2017, the contents of all of which are hereby incorporated by reference in their entireties.

FIELD OF THE INVENTION

The present invention relates to in situ generated catalyst bound alpha radical compound represented by formula (I) or (II) and a single pot process for the preparation of oxo compounds by using in situ generated catalyst bound alpha radical of formula (I) or (II).

BACKGROUND AND PRIOR ART OF THE INVENTION

Amides are useful and highly valuable compounds for the production of fine chemicals and pharmaceuticals. In terms of pharmaceutically important reactions, amide formation and oxidation ranks first and second spots with around 9 and 4 percent frequency. An improvement on those fronts in terms of reducing waste and cost will be of high importance. The amide bond formation from acid and amine suffers from using stoichiometric coupling reagents leading stoichiometric waste. Although a lot of improvements reported over the years in terms of efficiencies including catalytic activator, it is still a case of trials and error method to find the best coupling reagents for a particular amide formation.

On the other hand, aldehyde and amine form imine/iminium with the loss of water by just mixing the two reagents. Therefore, an easy oxidation of imine/iminium to amide will lead to the waste free formation of amide from aldehydes and amines; especially since aldehydes are important intermediates for many asymmetric transformations and typically oxidized to acid prior to amide synthesis. The "oxidation" of imine/iminium to amide falls into the second frequent chemical reaction. Oxidative coupling of aldehyde and amine to amide became one of the attractive methods for amide formation, but require high molecular weight stoichiometric oxidizing reagents yielding high volume waste. Other methods typically required stoichiometric oxidizing regents or expensive and toxic transition metal catalysts; a general problem associated with all oxidation reactions.

Article titled "Formation of amides from imines via cyanide-mediated metal-free aerobic oxidation" by HA Seo et al. published in *J. Org. Chem.*, 2015, 80 (24), pp 11993-11998 reports a new protocol for the direct formation of amides from imines derived from aromatic aldehydes via metal-free aerobic oxidation in the presence of cyanide. This protocol was applicable to various aldimines, and the desired amides were obtained in moderate to good yields. This procedure suffers from stoichiometric (110%, 1.1 equivalent) use of toxic cyanide, high temperature and applicable to secondary aryl amide formation only.

Article titled "*Phenazinium* salt-catalyzed aerobic oxidative amidation of aromatic aldehydes" by R Cadoni published in *Org. Lett.*, 2014, 16 (21), pp 5821-5815 reports a one-pot synthesis of amides from aldheydes and amines via photocatalytic aerobic oxidative method. Aromatic aldehydes and many aliphatic disubstituted amines are tolerant in this transformation.

The prior art processes for this transformation are handicapped by certain disadvantages, such as high temperatures, organic by-products, and soluble and/or expensive catalysts. Therefore, there remains a need for efficient, cost-effective process for the synthesis of amides. Accordingly, the present inventors developed an environment friendly, single pot process for the preparation of amides by using aerobic oxidation of imine or aldehyde and amine using in situ generated catalyst bound alpha radical.

OBJECTIVES OF THE INVENTION

The main objective of the present invention is to provide in situ generated catalyst bound alpha radical compound represented by formula (I) or (II).

Another objective of the present invention is to provide use of the compound of formula (I) or (II) for regio- and stereoselective aerobic oxidation and oxidative kinetic resolution.

Still another objective of the present invention is to provide a single pot process for the preparation of oxo compounds by using in situ generated catalyst bound alpha radical compound of formula (I) or (II) comprises subjecting an aerobic oxidation of aldehyde and amine or imine and alkyl halide/triflate by using in situ generated catalyst bound alpha radical compound of formula (I) or (II) in presence of suitable base at the temperature in the range of 0 to 30° C. to afford desired oxo compounds.

SUMMARY OF THE INVENTION

Accordingly, the present invention provides in situ generated catalyst bound alpha radical compound represented by formula (I) or (II);

$R^1$, $R^2$, $R^3$, $R^4$ and $R^5$ are selected from H, alkyl, aryl, alkene, alkoxy, amine, alkynyl, halides, CO, COOH, and $NO_2$ substituents;

CAT is selected from DBU, TBD, dialkylphosphites, thiophenol

R is selected from H, alkyl, aryl, alkene, alkoxy, amine, alkynyl, halides;

R, $R^1$, $R^2$, $R^3$, $R^4$ and $R^5$ may optionally forms a cyclic ring

The compound of formula (I) or (II) is used in regio- and stereoselective aerobic oxidation and oxidative kinetic resolution.

The present invention further provides a single pot process for the preparation of oxo compounds by using in situ generated catalyst bound alpha radical compound of formula (I) or (II) comprises subjecting an aerobic oxidation of aldehyde and amine or imine and alkyl halide/triflate by using in situ generated catalyst bound alpha radical compound of formula (I) or (II) in presence of suitable base at the temperature in the range of 0 to 30° C. to afford desired oxo compounds.

DETAILED DESCRIPTION OF THE INVENTION

The invention will now be described in detail in connection with certain preferred and optional embodiments, so that various aspects thereof may be more fully understood and appreciated.

In an embodiment, the present invention provides in situ generated catalyst bound alpha radical compound represented by formula (I) or (II);

Formula (I)

And/Or

Formula (II)

$R^1$, $R^2$, $R^3$, $R^4$ and $R^5$ are selected from H, alkyl, aryl, alkene, alkoxy, amine, alkynyl, halides, CO, COOH, and $NO_2$ substituents;

CAT is selected from DBU, TBD, dialkylphosphites, thiophenol;

DBU  TBD  Phosphites  Thiophenol

R is selected from H, alkyl, aryl, alkene, alkoxy, amine, alkynyl, halides;

R, $R^1$, $R^2$, $R^3$, $R^4$ and $R^5$ may optionally forms a cyclic ring

The compound in-situ intermediate of formula (I) or (II) is used in region- and stereoselective aerobic oxidation and oxidative kinetic resolution. Regio-selective when one of the substituents is alkene and stereoselective when one of the alkyl substituent on amine have a chiral center.

In another embodiment, the present invention provides a single pot process for the preparation of oxo compounds by using in situ generated catalyst bound alpha radical compound of formula (I) or (II) comprises subjecting an aerobic oxidation of aldehyde and amine or imine and alkyl halide/triflate by using in situ generated catalyst bound alpha radical compound of formula (I) or (II) in presence of suitable base at the temperature in the range of 0 to 30° C. to afford desired oxo compounds.

In a preferred embodiment, the process for the preparation of oxo compounds by using in situ generated catalyst bound alpha radical compound of formula (I) or (II) comprising the steps of:

a) forming of iminium salt by reacting aldehyde with amine in suitable solvent or by reacting imine with alkyl halide/triflate to form iminium salt A b) reacting nucleophile or catalyst with iminium salt A in suitable base to form neutral compound B c) forming radical of compound B to afford catalyst bound alpha radical compound of formula (I) or (II) followed by conversion into oxo compounds wherein steps (a) to (c) carried out at the temperature in the range of 0 to 30° C.

The radical formed via two pathways:

1) A base deprotonate the C—H to corresponding anion which reacts with oxygen to form radical.

2) B undergoes one electron oxidation with iminium salt A under household light. The radical cation formed loses one proton ($H^+$) in presence of base to form the radical.

The process for the preparation of oxo compounds by using in situ generated catalyst bound alpha radical compound of formula (I or II) as shown in following scheme:

Scheme 1

The present invention discloses imine reacts with alkyl halide/triflate to form imminium salt of compound (A). Imminium salt of A reacts with nucleophile or catalyst in suitable base to form compound B. Further from B alpha radical formation occurred to form catalyst bound alpha radical of B represented by formula (I) or (II).

Further, the present invention discloses aldehyde reacts with amine to form imminium salt of (compound) formula (A). Imminium salt of (compound) formula (A) reacts with nucleophile or catalyst in suitable base to form compound B. Further from B alpha radical formation occurred to form catalyst bound alpha radical of B represented by formula (I) or (II).

The reaction is carried out under oxygen atmosphere.

The imine is selected from aliphatic imine or aromatic imine or heteroaromatic imine.

The imine is selected from (E)-N,1-diphenylmethanimine or (E)-1-(2-chloro-6-fluorophenyl)-N-phenylmethanimine.

The alkyl triflate is methyl triflate and the alkyl halide is selected from methyl triflate, methyl iodide, ethyl bromide, allyl bromide or benzyl bromide.

The aldehyde is aromatic aldehyde, wherein aromatic aldehyde is selected from benzaldehyde or 2-chloro-6-fluoro-benzaldehyde.

The base is selected from 1,8-diazabicyclo(5.4.0)undec-7-ene(DBU), potassium carbonate, potassium hydroxide (KOH), potassium tert-butoxide (KO'Bu), lithium bis(trimethylsilyl)amide (LiHMDS), lithium diisopropymamide (LDA) or n-BuLi.

The nucleophile or catalyst is selected from 1,8-Diazabicyclo(5.4.0)undec-7-ene(DBU), 1,5,7-Triazabicyclo[4.4.0]dec-5-ene (TBD), dimethyl phosphite (DMHP), (1R,7R)-9,9-dimethyl-4-hydrido-4-oxo-2,2,6,6-tetramethyl-3,5,8,10 tetraoxa-4-phosphabicyclo[5.3.0]decane (P2), (1R,7R)-9,9-dimethyl-4-hydrido-4-oxo-2,2,6,6-tetraphenyl-3,5,8,10 tetraoxa-4-phosphabicyclo[5.3.0]decane (P3), (1R,7R)-9,9-dimethyl-4-hydrido-4-oxo-2,2,6,6-tetra(2-methylphenyl)-3,5,8,10-tetraoxa-4-phosphabicyclo[5.3.0]decane (P4), (1R,7R)-9,9-dimethyl-4-hydrido-4-oxo-2,2,6,6-tetra(3,5-dimethylphenyl)-3,5,8,10 tetraoxa-4-phosphabicyclo[5.3.0]decane (P5), (1R,7R)-9,9-dimethyl-4-hydrido-4-oxo-2,2,6,6-tetranapthyl-3,5,8,10 tetraoxa-4-phosphabicyclo[5.3.0]decane, diphenyl phosphite (P6), thiophenol.

The solvent is selected from tetrahydrofuran (THF), methyl tert-butyl ether (MTBE), acetonitrile (MeCN), dichloromethane (DCM), dichloroethane (DCE), chloroform ($CHCl_3$), dimethylformamide (DMF) or mixture thereof.

The compound A is selected from 2-benzyl-3,4-dihydroisoquinolin-2-ium tetrafluoroborate (A1-1), 2-phenyl-3,4-dihydroisoquinolin-2-ium tetrafluoroborate (A1-2), 2-(o- tolyl)-3,4-dihydroisoquinolin-2-ium tetrafluoroborate (A1-3), 2-(2-methoxyphenyl)-3,4-dihydroisoquinolin-2-ium tetrafluoroborate (A1-4), 2-(naphthalen-1-yl)-3,4-dihydroisoquinolin-2-ium tetrafluoroborate (A1-5), 2-Benzylisoquinolin-2-ium tetrafluoroborate (A2-1), 2-methylisoquinolin-2-ium tetrafluoroborate (A2-2), 2-allylisoquinolin-2-ium tetrafluoroborate (A2-3), 2-benzyl-5-nitroisoquinolin-2-ium tetrafluoroborate (A2-4), 2-benzyl-3-bromoisoquinolin-2-ium tetrafluoroborate (A2-5), 3-Bromo-2-methylisoquinolin-2-ium trifluoromethanesulfonate (A2-6), 2-Methy-3-phenyllisoquinolin-2-ium trifluoromethanesulfonate (A2-7), 4-Bromo-2-methylisoquinolin-2-ium trifluoromethanesulfonate (A2-8), 2-Methyl-4-(phenylethynyl)isoquinolin-2-ium trifluoromethanesulfonate (A2-9), 5-Methylphenanthridin-5-ium trifluoromethanesulfonate (A2-10), 2-Methylphthalazin-2-ium trifluoromethanesulfonate (A2-11), 2-Methyl-5-nitroisoquinolin-2-ium trifluoromethanesulfonate (A2-12), 2,6-Dimethylisoquinolin-2-ium trifluoromethanesulfonate (A2-13), 5,8-dibromo-2-methylisoquinolin-2-ium trifluoromethanesulfonate (A2-14), 2-(1-phenylethyl)isoquinolin-2-ium trifluoromethanesulfonate (A2-15), 6-methyl-2-(1-phenylethyl)isoquinolin-2-ium trifluoromethanesulfonate (A2-16), 1-benzylquinolin-1-ium tetrafluoroborate (A3-1), 1-methylquinolin-1-ium tetrafluoroborate (A3-2), 1-ethylquinolin-1-ium tetrafluoroborate (A3-3), 1-methyl-3-phenylquinolin-1-ium trifluoromethanesulfonate (A3-4), 3-bromo-1-methylquinolin-1-ium trifluoromethanesulfonate (A3-5), 3-(dimethylamino)-1-methylquinolin-1-ium trifluoromethanesulfonate (A3-6), 1,4-dimethylquinolin-1-ium trifluoromethanesulfonate (A3-7), 4-methoxy-1-methylquinolin-1-ium trifluoromethanesulfonate (A3-8), 1-methyl-5-nitroquinolin-1-ium trifluoromethanesulfonate (A3-9), 8-hydroxy-1-methylquinolin-1-ium trifluoromethanesulfonate (A3-10), 8-methoxy-1-methylquinolin-1-ium trifluoromethanesulfonate (A3-11), 8-(allyloxy)-1-methylquinolin-1-ium trifluoromethanesulfonate (A3-12), 1-methyl-8-nitroquinolin-1-ium trifluoromethanesulfonate (A3-13), 5,8-dibromo-1-methylquinolin-1-ium trifluoromethanesulfonate (A3-14), 8-bromo-1-methylquinolin-1-ium trifluoromethanesulfonate (A3-15), 2-(methoxycarbonyl)-1-methylquinolin-1-ium trifluoromethanesulfonate (A3-16), 10-methylacridin-10-ium trifluoromethanesulfonate (A3-17).

The compound B is selected from Dimethyl (2-benzyl-1,2,3,4-tetrahydroisoquinolin-1-yl)phosphonate(B1-1), Dimethyl (2-phenyl-1,2,3,4-tetrahydroisoquinolin-1-yl)phosphonate(B1-2), Dimethyl (2-(o-tolyl)-1,2,3,4-tetrahydroisoquinolin-1-yl)phosphonate(B1-3), Dimethyl (2-(2-methoxyphenyl)-1,2,3,4-tetrahydroisoquinolin-1-yl)phosphonate(B1-4), Dimethyl (2-(2-methoxyphenyl)-1,2,3,4-tetrahydroisoquinolin-1-yl)phosphonate(B1-4), Dimethyl (2-benzyl-1,2-dihydroisoquinolin-1-yl)phosphonate(B2-1), Dimethyl (2-methyl-1,2-dihydroisoquinolin-1-yl)phosphonate(B2-2), Dimethyl (2-allyl-1,2-dihydroisoquinolin-1-yl)phosphonate(B2-3), Dimethyl (2-benzyl-5-nitro-1,2-dihydroisoquinolin-1-yl)phosphonate(B2-4), Dimethyl (2-benzyl-3-bromo-1,2-dihydroisoquinolin-1-yl)phosphonate(B2-5), Dimethyl (3-bromo-2-methyl-1,2-dihydroisoquinolin-1-yl)phosphonate(B2-6), Dimethyl (2-methyl-3-phenyl-1,2-dihydroisoquinolin-1-yl)phosphonate(B2-7), Dimethyl (4-bromo-2-methyl-1,2-dihydroisoquinolin-1-yl)phosphonate(B2-8), Dimethyl (2-methyl-4-(phenylethynyl)-1,2-dihydroisoquinolin-1-yl)phosphonate(B2-9), Dimethyl (5-methyl-5,6-dihydrophenanthridin-6-yl)phosphonate(B2-10), Dimethyl (2-methyl-1,2-dihydrophthalazin-1-yl)phosphonate(B2-11), Dimethyl (2-methyl-5-nitro-1,2-dihydroisoquinolin-1-yl)phosphonate(B2-12), Dimethyl (2,6-dimethyl-1,2-dihydroisoquinolin-1-yl)phosphonate(B2-13), Dimethyl (5,8-dibromo-2-methyl-1,2-dihydroisoquinolin-1-yl)phosphonate(B2-14), Dimethyl (2-(1-phenylethyl)-1,2-dihydroisoquinolin-1-yl)phosphonate(B2-15), Dimethyl (6-methyl-2-(1-phenylethyl)-1,2-dihydroisoquinolin-1-yl)phosphonate(B2-16), 2,2-dimethyl-4,4,8,8-tetra(naphthalen-1-yl)-6-(2-(1-phenylethyl)-1,2-dihydroisoquinolin-1-yl)tetrahydro-[1,3]dioxolo[4,5-e][1,3,2]dioxaphosphepine 6-oxide(B2-17), 2,2-dimethyl-6-(6-methyl-2-(1-phenylethyl)-1,2-dihydroisoquinolin-1-yl)-4,4,8,8-tetra(naphthalen-1-yl)tetrahydro-[1,3]dioxolo[4,5-e][1,3,2]dioxaphosphepine 6-oxide(B2-18), -(4-bromo-2-methyl-1,2-dihydroisoquinolin-1-yl)-2,2,4,4,8,8-hexamethyltetrahydro-[1,3]dioxolo[4,5-e][1,3,2]dioxaphosphepine 6-oxide(B2-19), 2-Benzyl-1-(phenylthio)-1,2-dihydroisoquinoline(B2-20), Diphenyl (2-benzyl-1,2-dihydroisoquinolin-1-yl)phosphonate(B2-26), 1-(2-benzyl-1,2-dihydroisoquinolin-1-yl)-2,3,4,6,7,8,9,10-octahydropyrimido[1,2-a]azepin-1-ium(B2-21), 1-(2-benzyl-1,2-dihydroisoquinolin-1-yl)-3,4,6,7,8,9-hexahydro-2H-pyrimido[1,2-a]pyrimidin-1-ium (B2-22), 1-(2-methyl-1,2-dihydroisoquinolin-1-yl)-3,4,6,7,8,9-hexahydro-2H-pyrimido[1,2-a]pyrimidin-1-ium(B2-23), 1-(2-methyl-1,2-dihydroisoquinolin-1-yl)-2,3,4,6,7,8,9,10-octahydropyrimido[1,2-a]azepin-1-ium(B2-24), 2-methyl-1-(phenylthio)-1,2-dihydroisoquinoline(B-25), Dimethyl (1-benzyl-1,2-dihydroquinolin-2-yl)phosphonate (B3-1), Dimethyl (1-methyl-1,2-dihydroquinolin-2-yl)phosphonate (B3-2), Dimethyl (1-ethyl-1,2-dihydroquinolin-2-yl)phosphonate (B3-3), Dimethyl (1-methyl-3-phenyl-1,2-dihydroquinolin-2-yl)phosphonate (B3-4), 1-(3-bromo-1-methyl-1,2-dihydroquinolin-2-yl)-2,3,4,6,7,8,9,10-octahydropyrimido[1,2-a]azepin-1-ium (B3-5), Dimethyl (3-(dimethylamino)-1-methyl-1,2-dihydroquinolin-2-yl)phosphonate (B3-6), Dimethyl (1,4-dimethyl-1,2-dihydroquinolin-2-yl)phosphonate (B3-7), Dimethyl (4-methoxy-1-methyl-1,2-dihydroquinolin-2-yl)phosphonate (B3-8), Dimethyl (1-methyl-5-nitro-1,2-dihydroquinolin-2-yl)phosphonate (B3-9), Dimethyl (8-hydroxy-1-methyl-1,2-dihydroquinolin-2-yl)phosphonate (B3-10), Dimethyl (8-methoxy-1-methyl-1,2-dihydroquinolin-2-yl)phosphonate (B3-11), Dimethyl (8-(allyloxy)-1-methyl-1,2-dihydroquinolin-2-yl)phosphonate (B3-12), Dimethyl (1-methyl-8-nitro-1,2-dihydroquinolin-2-yl)phosphonate (B3-13), Dimethyl (5,8-dibromo-1-methyl-1,2-dihydroquinolin-2-yl) phosphonate (B3-14), Dimethyl (5,8-dibromo-1-methyl-1,4-dihydroquinolin-4-yl)phosphonate (B3-18), Dimethyl (8-bromo-1-methyl-1,2-dihydroquinolin-2-yl)phosphonate (B3-15), Dimethyl (8-bromo-1-methyl-1,4-dihydroquinolin-4-yl)phosphonate (B3-19), Methyl 4-(dimethoxyphosphoryl)-1-methyl-1,4-dihydroquinoline-2-carboxylate (B3-16), Dimethyl (10-methyl-9,10-dihydroacridin-9-yl) phosphonate (B3-17) or dimethyl ((methyl(phenyl)amino)(phenyl)methyl)phosphonate (B5).

The oxo compound is selected from 3,4-dihydro-2-benzylisoquinolin-1(2H)-one (O1-1), 2-phenyl-3,4-dihydroisoquinolin-1(2H)-one (O1-2), 2-(o-tolyl)-3,4-dihydroisoquinolin-1(2H)-one (O1-3), 2-(2-methoxyphenyl)-3,4-dihydroisoquinolin-1(2H)-one (O1-4), 2-(naphthalen-1-yl)-3,4-dihydroisoquinolin-1(2H)-one (O1-5), 2-benzylisoquinolin-1(2H)-one (O2-1), 2-methylisoquinolin-1(2H)-one (O2-2), 2-benzyl-5-nitroisoquinolin-1(2H)-one (O2-3), 2-benzyl-3-bromoisoquinolin-1(2H)-one (O2-4), 2-allylisoquinolin-1(2H)-one (O2-5), 3-bromo-2-methylisoquinolin-1(2H)-one (O2-7), 2-methyl-3-phenylisoquinolin-1(2H)-one (O2-8), 4-bromo-2-methylisoquinolin-1(2H)-one (O2-9), 2-methyl-4-(phenylethynyl)isoquinolin-1(2H)-one (O2-10), 5-methylphenanthridin-6(5H)-one (O2-11), 2-methylphthalazin-1(2H)-one (O2-12), 2-methyl-5-nitroisoquinolin-1(2H)-one (O2-13), 2,6-dimethylisoquinolin-1(2H)-one (O2-14), 5,8-dibromo-2-methylisoquinolin-1(2H)-one (O2-15), (S)-2-(1-phenylethyl)isoquinolin-1(2H)-one (O2-16), 1-benzylquinolin-2(1H)-one (O3-1), 1-methylquinolin-2(1H)-one (O3-2), 1-ethylquinolin-2(1H)-one (O3-3), 1-methyl-3-phenylquinolin-2(1H)-one (O3-4), 3-bromo-1-methylquinolin-2(1H)-one (O3-5), 3-(dimethylamino)-1-methylquinolin-2(1H)-one (O3-6), 1,4-dimethylquinolin-2(1H)-one (O3-7), 4-methoxy-1-methylquinolin-2(1H)-one (O3-8), 1-methyl-5-nitroquinolin-2(1H)-one (O3-9), 8-hydroxy-1-methylquinolin-2(1H)-one (O3-10), 8-methoxy-1-methylquinolin-2(1H)-one (O3-11), 8-(allyloxy)-1-methylquinolin-2(1H)-one (O3-12), 1-methyl-8-nitroquinolin-2(1H)-one (O3-13), 5,8-dibromo-1-methylquinolin-2(1H)-one (O3-14), 8-bromo-1-methylquinolin-2(1H)-one (O3-15), 5,8-dibromo-1-methylquinolin-4(1H)-one (O4-14), 8-bromo-1-methylquinolin-4(1H)-one (O4-15) or methyl 1-methyl-4-oxo-1,4-dihydroquinoline-2-carboxylate (O4-1) or 10-methylacridin-9(10H)-one (O4-2).

Prior art documents does not disclose the generation of in situ generated catalyst bound alpha radical compound represented by formula (I) or (II) and also the reaction is transition metal free. These features make invention novel and non-obvious.

The present invention provides different iminium salt that can be auto-oxidized by air in presence of a suitable base to form regio- and stereoselective oxidation products via nucleophile attached alpha-radical intermediacy.

The iminium ion which is a part of heteroaromatic system and is also oxidized regioselectively (and stereoselectively). The iminium salt (A) formation and oxidation can be done in one-pot, or the salts can be isolated and stored. The whole operation can be done under ambient condition.

The anionic phosphite catalyst added initial intermediates (B) are characterized in few cases. These intermediates from heteroaromatic compounds are unstable to silica column separation but stable for in-situ characterization via NMR. Two of the in-situ $^1$H-NMR are taken.

The corresponding intermediates (B) with non-heteroaromatic compounds (cyclic or acyclic iminium) are stable to silica column isolation and characterized after silica column purification.

Oxidation under radical quenching reagent Butylated hydroxytoluene (BHT) is performed which resulted in no oxidation. The radical quencher BHT is known to quench any radicals, and present invention proposed radical intermediate of formula I or II would also be quenched without reacting with oxygen for oxidation.

Emission spectrum of intermediate (20×10$^{-5}$ M in dichloromethane, $\lambda_{ex}$=380 nm) is studied with different amounts of added salt. The emission reduces with salt concentration, and longer time lapse resulted in higher reduction.

B undergoes one electron oxidation with iminium salt A under household light. The radical cation formed loses one proton (H$^+$) in presence of base to form the radical.

Figure 1:
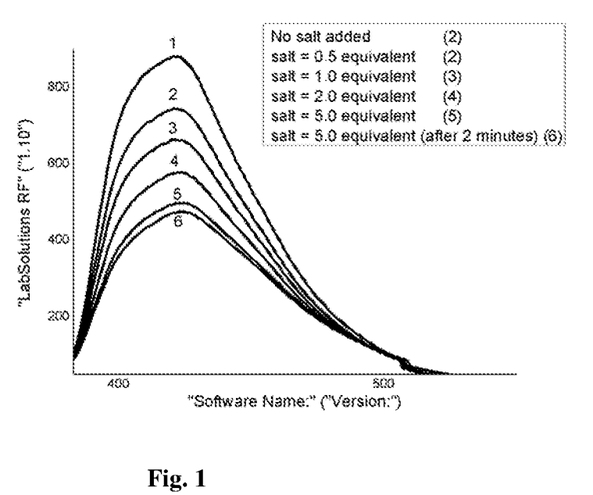
FIG. 1: Quenching study

FIG. 1 shows A absorb the light emitted from B (The light intensity decreases in presence of increasing concentration of A, and with longer time).

Figure 2:
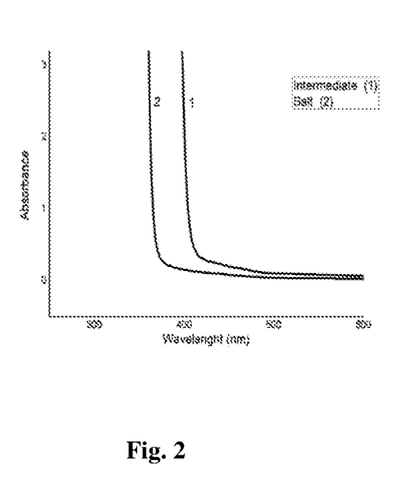
FIG. 2: UV-vis absorption spectrum of 2-(1-phenylethyl)isoquinolin-2-ium trifluoromethanesulfonate (1A-15) and its intermediate with dimethylphosphite (1B-15). Absorption spectrum of Salt and intermediate (C=0.03 M) in dichloromethane.

FIG. 2 shows A do not absorb household light but B absorb.

Figure 3:
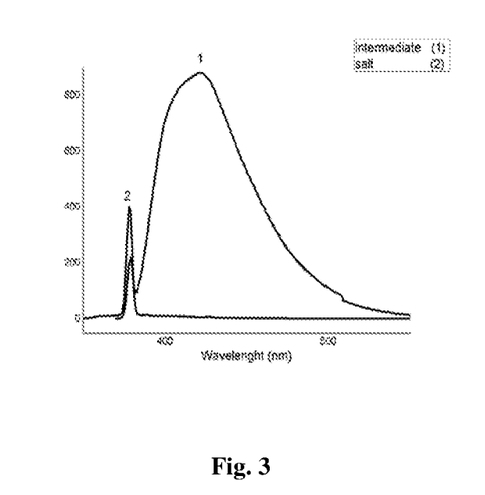
FIG. 3: Emission spectrum of 2-(1-phenylethyl)isoquinolin-2-ium trifluoromethanesulfonate (1A-15) and its intermediate with dimethylphosphite (1B-15). Emission spectrum of Salt and intermediate (20×10-5 M in dichloromethane, $\lambda_{ex}$=380 nm). Salt has zero emission.

FIG. 3 shows A do not emit any light but B emit light (fluorescence) when absorb household light These three figures provide evidences that B oxidize to radical cation by giving one electron to A under household light.

The visible light photoredox method for oxidation is well-established in literature to undergo via radical intermediate. No reaction in the dark under photoredox condition also indicates formation of a radical intermediate of formula I or II for oxidation. Light is known to excite one electron to form a radical intermediate. In the present case performed visible light absorption of intermediate B, its emission after absorption (fluorescence), and absorption of fluorescence emission of B by the salt A. These absorption/emission/absorption matches with present self-photoredox mechanism via intermediate of formula I or II. Prior art do not undergo oxidation via intermediate I or II. Since intermediate I or II contains catalyst, the present invention is able to control the oxidation process which was not achieved earlier.

One of the photoredox oxidation reactions is monitored via $^1$H and $^{31}$P NMR with both stoichiometric and 10 mol % catalyst. The 10 mol % catalyst reaction showed the catalyst to be present in the form of catalyst added intermediate of type B after completing 6-8 oxidation cycle.

In still another embodiment, the present invention provides catalyst stability under oxidation condition. Reaction is carried out in different conditions. Refer Scheme 2, 3 and 4.

$^{31}$P NMR monitoring of the reaction with substrate showed that the catalyst remains as two diastereomeric phosphate intermediates even after 6-8 catalytic cycles without any noticeable decomposition (oxidative degradation).

In Scheme 2, $^{31}$P NMR was taken when the catalyst is free catalyst. That give the value ~0 which is characteristic for catalyst P2.

In scheme 3, run the reaction with 1 equivalent of catalyst. Since the catalyst added slowly to A to form B, still observe ~0 for free P2 catalyst as well as ~12 for B (two peak very close to each other, due to diastereomer).

In scheme 4, crude was taken $^{31}$P NMR after the reaction is completed with 10 mol % catalyst. The peaks ~12 (two close peaks for diastereomer) indicate the catalyst remained intact as B.

Scheme 2

$^1$H and $^{31}$P-NMR studies (crude in CDCl$_3$ after solvent removal): 10 mol % phosphite (P2), isoqunolinium salt (A2-8), K$_2$CO$_3$ (6.0 equiv.), MTBE, 40° C., 30 h. ~65% product formation indicate 6-7 catalytic cycle. Only phosphite bound intermediate (~1:1 dr) indicate no catalyst oxidation.

Following examples are given by way of illustration therefore should not be construed to limit the scope of the invention.

EXAMPLES: GENERAL EXAMPLE

The salts were prepared by mixing the heteroaromatic compounds or imine with corresponding alkyl bromide/iodide/triflate at appropriate solvent and temperature. A counter anion exchange was done for some alkyl halide cases with excess sodium tetrafluoroborate in acetone as solvent.

Example 1: Imminium Salt Synthesis

Methyl Trifluoromethanesulfonate Salt:

To a flame dried 50 ml round-bottom flask under argon atmosphere, isoquinoline or quinoline derivatives (2.0 mmol, 1.0 equiv) was taken followed by dry DCM (10 ml). The solution was cooled to 0° C., and methyl trifluoromethanesulfonate (3.0 mmol, 1.5 equiv) was added dropwise via syringe. The reaction mixture was slowly warmed at 35° C. with TLC monitoring. Upon consumption of starting material, DCM was removed under reduced pressure, and the residue was washed with diethyl ether (3-5 times) to remove low polar impurities to obtain pure salt.

For non-heteroaromatic imine starting material, the product iminium is not hydrolytically stable and the following catalytic oxidation was done in same pot without isolation.

A. Synthesis of 3-Bromo-2-methylisoquinolin-2-ium Trifluoromethanesulfonate (A2-6)

Obtained as a white solid (667.8 mg, 90% yield). R$_f$ (MeOH/DCM=05:95)=0.4; MP=139.4° C. $^1$H NMR (400 MHz, DMSO-d$_6$) δ 4.45 (s, 3H), 8.17 (t, J=7.02 Hz, 1H), 8.31-8.47 (m, 2H), 8.55 (d, J=8.54 Hz, 1H), 9.24 (s, 1H), 10.07 (s, 1H). $^{13}$C NMR (DMSO-d$_6$, 100 MHz) δ 47.93, 120.95, 125.89, 127.22, 131.36, 132.06, 135.45, 137.24, 138.52, 150.82. FTIR (cm$^{-1}$): 3125, 3036, 2286, 1856, 1703, 1636, 1559, 1462, 1341, 1274, 1149, 1028. HRMS: Calculated for C$_{10}$H$_9$NBr [M]$^+$: 221.9913, found: 221.9916.

B. Synthesis of 2,6-Dimethylisoquinolin-2-ium Trifluoromethanesulfonate (A2-13)

Obtained as a brown solid (595 mg, 97% yield). R$_f$ (MeOH/DCM=05:95)=0.4; MP=118.2° C. $^1$H NMR (400 MHz, DMSO-d$_6$) δ 2.66 (s, 3H), 4.44 (s, 3H), 7.92 (d, J=8.39 Hz, 1H), 8.12 (s, 1H), 8.37 (d, J=8.39 Hz, 1H), 8.42 (d, J=6.48 Hz, 1H), 8.64 (d, J=6.49 Hz, 1H), 9.88 (s, 1H). $^{13}$C NMR (DMSO-d$_6$, 100 MHz) δ 22.17, 47.62, 124.54, 125.39, 125.99, 129.85, 133.30, 135.91, 136.85, 148.33, 149.94. FTIR (cm$^{-1}$): 3057, 2723, 2289, 1646, 1616, 1575, 1456, 1265, 1156, 1030. HRMS: Calculated for $C_{11}H_{12}N$ [M]+: 158.0966, found: 158.0964.

C. Synthesis of 5,8-dibromo-2-methylisoquinolin-2-ium trifluoromethanesulfonate (A2-14)

Obtain as a light brown solid (1.15 gm, 85% yield). $R_f$ (MeOH/DCM=05:95)=0.4; MP=159.5° C. $^1$H NMR (500 MHz, DMSO-$d_6$) δ 4.61 (s, 3H), 8.30 (d, J=8.01 Hz, 1H), 8.48 (d, J=8.01 Hz, 1H), 8.66 (d, J=6.87 Hz, 1H), 8.90 (d, J=7.63 Hz, 1H), 10.03 (s, 1H). $^{13}$C NMR (DMSO-$d_6$, 125 MHz) δ 48.33, 120.74, 123.39, 125.01, 127.58, 135.82, 137.43, 138.82, 140.37, 150.76. FTIR (cm$^{-1}$): 3071, 3036, 2298, 1932, 1647, 1582, 1547, 1458, 1265, 1220, 1155, 1031. HRMS: Calculated for $C_{10}H_8NBr^{81}Br$ [M]$^+$: 301.8998, found: 301.8995.

D. Synthesis of 1-methyl-3-phenylquinolin-1-ium Trifluoromethanesulfonate (A3-4)

Obtained as a White Solid (199 mg, 54% yield). $R_f$ (Methanol/DCM=10:90)=0.2; MP=181.6° C. $^1$H NMR (500 MHz, DMSO-$d_6$) δ 4.72 (s, 3H), 7.56-7.64 (m, 1H), 7.64-7.71 (m, 2H), 8.03 (d, J=7.25 Hz, 2H), 8.09 (t, J=7.63 Hz, 1H), 8.18-8.35 (m, 1H), 8.53 (d, J=8.77 Hz, 1H), 8.49 (d, J=8.01 Hz, 1H), 9.62 (s, 1H), 9.91-10.02 (m, 1H). $^{13}$C NMR (125 MHz, DMSO-$d_6$) δ 45.86, 119.42, 127.87, 129.69, 130.03, 130.31, 130.68, 131.00, 133.89, 133.99, 135.64, 137.65, 143.37, 149.82. FTIR (cm$^{-1}$): 2985, 2885, 1538, 1387, 1246, 1142, 1029, 764, 694, 638. HRMS: Calculated for $C_{16}H_{14}N$ [M]$^+$: 220.1121, found: 220.1121.

E. Synthesis of 3-(dimethylamino)-1-methylquinolin-1-ium Trifluoromethanesulfonate (A3-6)

Obtained as a yellow Solid (376 mg, 56% yield). $R_f$ (Methanol/DCM=10:90)=0.3; MP=134° C. $^1$H NMR (500 MHz, DMSO-$d_6$) δ 3.17 (s, 6H), 4.62 (s, 3H), 7.75-7.90 (m, 2H), 8.08-8.17 (m, 1H), 8.17-8.31 (m, 2H), 9.20 (d, J=2.67 Hz, 1H). $^{13}$C NMR (125 MHz, DMSO-$d_6$) δ 28.98, 45.35, 118.42, 121.12, 127.93, 129.53, 129.62, 130.24, 131.22, 139.04, 143.73. FTIR (cm$^{-1}$): 3058, 1619, 1538, 1390, 1267, 1137, 1020, 879, 765, 629. HRMS: Calculated for $C_{12}H_{15}N_2$ [M]$^+$: 187.1230, found: 187.1231.

F. Synthesis of 8-(allyloxy)-1-methylquinolin-1-ium Trifluoromethanesulfonate (A3-12)

Obtained as a White powder (500 mg, 71% yield). $R_f$ (Methanol/DCM=10:90)=0.6; MP=108° C. $^1$H NMR (500 MHz, DMSO-$d_6$) δ 4.83 (s, 3H), 4.92 (d, J=5.34 Hz, 2H), 5.40 (d, J=10.68 Hz, 1H), 5.47-5.61 (m, 1H), 6.11-6.30 (m, 1H), 7.78 (d, J=7.63 Hz, 1H), 7.92 (t, J=8.01 Hz, 1H), 7.98 (d, J=8.01 Hz, 1H), 8.09 (dd, J=8.20, 5.91 Hz, 1H), 9.18 (d, J=8.39 Hz, 1H), 9.32 (d, J=5.72 Hz, 1H). $^{13}$C NMR (126 MHz, DMSO-$d_6$) δ 52.46, 71.59, 118.08, 119.64, 122.60, 122.81, 130.75, 130.97, 132.21 132.85, 147.61, 150.54, 152.37. FTIR (cm$^1$): 3073, 2984, 1603, 1529, 1383, 1244, 1149, 1023, 918, 880, 749, 626. HRMS: Calculated for $C_{13}H_{14}NO$ [M]$^+$: 200.1070, found: 200.1069.

G. Synthesis of 5,8-dibromo-1-methylquinolin-1-ium Trifluoromethanesulfonate (A3-14)

Obtained as a White Solid (1100 mg, 50% yield). $R_f$ (Methanol/DCM=10:90)=0.4; 107.2° C. $^1$H NMR (400 MHz, DMSO-$d_6$) δ 4.98 (s, 3H), 8.16-8.37 (m, 2H), 8.52 (d, J=8.55 Hz, 1H), 9.45 (d, J=8.54 Hz, 1H), 9.60 (d, J=5.49 Hz, 1H). $^{13}$C NMR (100 MHz, DMSO-$d_6$) δ 52.53, 111.52, 124.38, 124.61, 131.28, 134.68, 139.17, 143.35, 147.95, 155.20. FTIR (cm$^{-1}$): 3033, 1576, 1511, 1382, 1252, 1148, 1029, 842, 751, 637. HRMS: Calculated for $C_{10}H_8Br_2N$ [M]$^+$: 301.8998, found: 301.8999.

H. Synthesis of 8-bromo-1-methylquinolin-1-ium Trifluoromethanesulfonate (A3-15)

Obtained as a White solid (175 mg, 47% yield). $R_f$ (Methanol/DCM=10:90)=0.15; MP=140.9° C. $^1$H NMR (500 MHz, DMSO-$d_6$) δ 4.99 (s, 3H), 7.87 (br. s, 1H), 8.08-8.28 (m, 1H), 8.48 (d, J=7.25 Hz, 1H), 8.53-8.72 (m, 1H), 9.33 (d, J=8.39 Hz, 1H), 9.51 (d, J=5.72 Hz, 1H). $^{13}$C NMR (126 MHz, DMSO-$d_6$) δ 52.21, 111.21, 122.98, 130.78, 131.96, 132.85, 137.50, 143.64, 149.48, 154.56. FTIR (cm$^{-1}$): 2972, 1543, 1243, 1226, 1135, 1029, 845, 757, 629. HRMS: Calculated for $C_{10}H_9BrN$ [M]$^+$: 221.9913, found: 221.9916.

I. Synthesis of 2-(methoxycarbonyl)-1-methylquinolin-1-ium Trifluoromethanesulfonate (A3-16)

Obtained as a white solid (76 mg, 22% yield). $R_f$ (Methanol/DCM=10:90)=0.25; MP=143.9° C. $^1$H NMR (500 MHz, DMSO-$d_6$) δ 4.15 (s, 3H), 4.67 (s, 3H), 8.15 (t, J=7.44 Hz, 1H), 8.40 (t, J=8.01 Hz, 1H), 8.48 (d, J=8.39 Hz, 1H), 8.55 (d, J=8.01 Hz, 1H), 8.69 (d, J=9.16 Hz, 1H), 9.48 (d, J=8.39 Hz, 1H). $^{13}$C NMR (125 MHz, DMSO-$d_6$) δ 43.30, 55.56, 120.49, 122.59, 130.41, 131.02, 131.37, 137.52, 139.96, 147.88, 149.14, 161.51. FTIR (cm$^{-1}$): 2985, 1749, 1442, 1385, 1264, 1151, 1027, 947, 854, 777, 635. HRMS: Calculated for $C_{12}H_{12}NO_2$ [M]$^+$: 202.0863, found: 202.0864.

Example 2

Alkyl Tetrafluoroborate Salt:

To a flame dried 50 ml round-bottom flask under argon atmosphere, isoquinoline or quinoline derivatives (5.0 mmol, 1.0 equiv) was dissolved in dry acetone (30 ml) at 35° C. To this solution, benzyl bromide (10.0 mmol, 2.0 equiv) was added followed by sodium tetrafluroborate (30.0 mmol, 6.0 equiv) and stirred at 35° C. The TLC analysis shows two polar spots with major low polar one. The reaction stopped after no further change in relative intensities for those polar spots, and the precipitate was removed by filtration. The solvent was removed under reduced pressure, and the residual solid was purified via silica column chromatography by 5:95 MeOH/DCM as eluent to obtain tetrafluoroborate salt.

A. Synthesis of 2-allylisoquinolin-2-ium Tetrafluoroborate (A2-3)

Obtained as a brown color solid (1.028 gm, 80% yield). $R_f$ (MeOH/DCM; 05:95)=0.4; MP=99-101° C. $^1$H NMR (500 MHz, DMSO-$d_6$) δ 5.40 (d, J=6.10 Hz, 2H), 5.46-5.59 (m, 2H), 6.16-6.37 (m, 1H), 8.10 (t, J=16.04 Hz, 1H), 8.29 (t, J=14.88 Hz, 1H), 8.37 (d, J=8.39 Hz, 1H), 8.54 (d, J=8.01 Hz, 1H), 8.62 (d, J=6.87 Hz, 1H), 8.73 (d, J=8.05, 1H), 10.04 (s, 1H). $^{13}$C NMR (DMSO-$d_6$, 125 MHz) δ 62.46, 122.10, 125.98, 127.27, 130.45, 131.23, 131.47, 134.75, 137.00, 137.06, 150.06. FTIR (cm$^{-1}$): 3022, 2928, 1590, 1216, 767. HRMS: Calculated for $C_{12}H_{12}N$ [M]$^+$: 170.0970, found: 170.0977.

129.79, 130.66, 135.58, 137.13, 147.11, 149.30. FTIR (cm$^{-1}$): 2914, 2845, 1592, 1524, 1434, 1358, 803, 766, 731. HRMS: Calculated for $C_{11}H_{12}N$ [M]$^+$: 158.0966, found: 158.0966.

Example 3: Dimethyl (2-methyl-1,2-dihydroisoquinolin-1-yl)phosphonate (B2-2)

$^1$H NMR (200 MHz, CDCl$_3$) δ 3.04 (d, J=3.28 Hz, 3H), 3.57 (d, J=10.38, 3H), 3.64 (d, J=10.38 Hz, 3H), 4.81 (d, J=8.59 Hz, 1H), 5.30 (dd, J=7.33, 2.53 Hz, 1H), 6.09 (dd, J=7.33, 1.14 Hz, 1H), 6.86 (d, J=7.07 Hz, 1H), 6.93-7.22 (m, 3H).

Example 4: Dimethyl (2-benzyl-1,2-dihydroisoquinolin-1-yl)phosphonate(B2-1)

$^1$H NMR (200 MHz, CDCl$_3$) δ 3.63 (dd, J=16.23, 10.42 Hz, 6H), 4.38 (d, J=15.54, 1H), 4.51-4.72 (m, 1H), 4.84 (dd, J=8.40, 0.44 Hz, 1H), 5.33-5.38 (m, 1H), 6.20-6.24 (m, 1H), 6.87-7.14 (m, 4H), 7.26-7.32 (m, 5H).

Example 5: Oxidation Procedures

Procedure A:
Salt was taken in a round bottom flask with MTBE (Methyl tert-butyl ether) solvent and purged with oxygen. Then 1.2 equivalents DBU added to it and stirred under an oxygen balloon at appropriate temperature until starting salt consumed (24 to 72 h). Solvent was removed in rotary evaporator and directly charge in flash silica gel column to purify the oxo-product.

Procedure B:
MeCN (3 ml) was added to a dry 10 ml reaction tube containing quinolinium salt (0.3 mmol) under argon and stirred at room temperature for 10-15 min until the salt dissolved. Dry oxygen was purged through the solution via a balloon and long needle for 5 min and cooled to 0° C. under $O_2$ balloon. To the above mixture dimethyl phosphite (50 mol %) was added followed by $K_2CO_3$ (3 equiv) and stirred for 2 h. Then KOH (3-7 equiv) or KO$^t$Bu (3 equiv) was added to it at once and slowly brought to 35° C. with TLC monitoring for the consumption of starting salt. Upon completion, saturated sodium chloride solution (5 ml) was added to quench the reaction, and the organic layer was extracted with ethyl acetate (3 times). The combined organic layer was dried over anhydrous sodium sulfate, and the solvent was removed under reduced pressure to obtain the crude which was filtered through a 6-inch silica column to get the desired product in pure form.

Procedure C:
THF (3 ml) was added to a dry 25 ml round bottom flask containing isoquinolinium salt (0.3 mmol) under argon and stirred at room temperature for 10-15 min until most of the salt dissolved. Dry oxygen was purged through the solution via a balloon and long needle for 5 min and cooled it to 0° C. under $O_2$ balloon. To the above mixture dimethyl phosphite (0.15 mmol, 50 mol %) was added followed by LiHMDS (1M solution in THF, 50 mol %) and stirred for 3 h. Then second LiHMDS (3 equiv) solution was added to it dropwise over a period of 6 hours at 0° C. via gas tight syringe, with TLC monitoring for the consumption of starting salt. Upon completion, saturated sodium chloride solution (5 ml) was added to quench the reaction, and the organic layer was extracted with ethyl acetate (3 times). The combined organic layer was dried over anhydrous sodium sulfate, and the solvent was removed under reduced pressure to obtain the crude which was filtered through a 6-inch silica column to get the desired product in pure form.

Procedure D:
Appropriate solvent (3 ml) was added to a dry 25 ml round bottom flask containing isoquinolinium salt (0.3 mmol) under air and stirred at 35° C. for 10-15 min until most of the salt dissolved. To the above mixture a particular phosphite catalyst (0.06 mmol, 20 mol %) was added followed by a weak base ($K_2CO_3$ or DABCO, 3 equiv) and stirred at appropriate temperature with tlc monitoring. Upon completion (or ~50% conversion for kinetic resolution), saturated sodium chloride solution (5 ml) was added to quench the reaction, and the organic layer was extracted with ethyl acetate (3 times). The combined organic layer was dried over anhydrous sodium sulfate, and the solvent was removed under reduced pressure to obtain the crude which was filtered through a 6-inch silica column to get the desired product in pure form. The chiral products were analyzed in HPLC with chiral IA column and n-hexane and IPA as eluent.

A. Synthesis of 2-Benzylisoquinolin-1(2H)-one (O2-1)

Starting with 1 mmol (307 mg)
Procedure A:
Yield 72%; Procedure B: yield 0%; Procedure C: yield 79%.

Melting point: 67-68° C. $^1$H NMR (400 MHz, CDCl$_3$) δ ppm 8.47 (d, J=7.6 Hz, 1H), 7.63 (t, J=7.2 Hz, 1H), 7.52-7.46 (m, 2H), 7.43-7.26 (m, 5H), 7.08 (d, J=7.6 Hz, 1H), 6.48 (d, J=7.2 Hz, 1H), 5.23 (s, 2H); $^{13}$C NMR (400 MHz, CDCl$_3$) δ ppm 162.38, 137.09, 136.99, 132.34, 131.40, 128.91, 128.16, 128.05, 127.92, 127.01, 126.39, 126.03, 106.57, 51.79; IR: 3070, 3020, 2943, 1646, 1624 cm$^{-1}$; HRMS: calcd. for [M+H]$^+$ $C_{16}H_{14}NO$: 236.1075, found: 236.1070.

B. Synthesis of 2-Benzyl-5-nitroisoquinolin-1(2H)-one (O2-3)

Both procedure A and C. O2-3 (27 mg, 48%). Melting point: 162-163° C.
$^1$H NMR (400 MHz, CDCl$_3$) δ ppm 8.81 (d, J=7.2 Hz, 1H), 8.41 (d, J=6.8 Hz, 1H), 7.58 (t, J=7.2 Hz, 1H), 7.33-7.30 (m, 7H), 5.24 (s, 2H); $^{13}$C NMR (400 MHz, CDCl$_3$) δ ppm 160.79, 144.71, 135.98, 135.10, 134.62, 130.89, 129.52, 129.10, 128.35, 128.26, 128.18, 125.92, 101.00, 52.17; IR: 3067, 2362, 1654, 1620, 1509, 1307 cm$^{-1}$; HRMS: calcd. for [M+H]$^+$ $C_{16}H_3N_2O_3$: 281.0926, found: 281.0921.

C. Synthesis of 2-Benzyl-3-bromoisoquinolin-1(2H)-one (O2-4)

Both procedure A and C; 02-4 (33 mg, 53%).
$^1$H NMR (200 MHz, CDCl$_3$) δ ppm 5.21 (s, 2H) 7.27-7.35 (m, 5H) 7.36 (s, 1H) 7.57 (ddd, J=8.08, 6.69, 1.64 Hz, 1H) 7.68-7.86 (m, 2H) 8.42-8.55 (m, 1H); HRMS: calcd. for [M+H]$^+$ C$_{16}$H$_{13}$BrNO: 314.0180, found: 314.0175.

D. Synthesis of 2-allylisoquinolin-1(2H)-one (O2-5) Via Procedure C

Obtained as a colorless liquid (39 mg, 71% yield). R$_f$ (Ethyl acetate/Pet. Ether; 20:80); =0.25. $^1$H NMR (400 MHz, CDCl$_3$) δ 4.65 (d, J=6.10 Hz, 2H), 5.08-5.33 (m, 2H), 5.98 (qd, J=11.09, 5.80 Hz, 1H), 6.51 (d, J=7.32 Hz, 1H), 7.05 (d, J=7.32 Hz, 1H), 7.40-7.56 (m, 2H) 7.63 (t, J=7.32 Hz, 1H), 8.44 (d, J=7.93 Hz, 1H). $^{13}$C NMR (100 MHz, CDCl$_3$) δ 50.62, 106.19, 117.92, 125.83, 126.18, 126.77, 127.89, 131.05, 132.12, 132.80, 136.97, 161.91. FTIR (cm$^-$$_1$): 3062, 2972, 1625, 1445, 1228, 682. HRMS: Calculated for C$_{12}$H$_{12}$NO [M+H]$^+$: 185.0919, found: 185.0925.

E. Synthesis of 2-methyl-3-phenylisoquinolin-1(2H)-one (O2-7) Via Procedure C Obtained as a white solid (48 mg, 68% yield). R$_f$ (Ethyl acetate/Pet. ether=50:50)=0.6; MP=178.9° C. $^1$H NMR (500 MHz, CDCl$_3$) δ 3.67 (s, 3H), 7.06 (s, 1H), 7.40-7.45 (m, 3H), 7.46-7.52 (m, 2H), 7.52-7.58 (m, 2H), 7.58-7.63 (m, 1H), 8.54 (d, J=8.01 Hz, 1H). $^{13}$C NMR (CDCl$_3$, 125 MHz) δ 37.02, 119.53, 124.62, 125.88, 126.87, 127.67, 128.04, 128.64, 129.94, 131.46, 131.95, 136.29, 136.39, 162.15. FTIR (cm$^{-1}$): 2927, 2859, 1621, 1425, 1035. HRMS: Calculatedfor C$_{16}$H$_{14}$NO [M+H]$^+$: 236.1070, found: 236.1070.

F. Synthesis of 2-methyl-4-(phenylethynyl)isoquinolin-1(2H)-one (O2-9) Via Procedure C Obtained as light yellow solid (47 mg, 60% yield). R$_f$ (Ethyl acetate/Pet. ether=50:50)=0.6; MP=120.2° C. $^1$H NMR (400 MHz, CDCl$_3$) δ 3.64 (s, 3H), 7.37-7.39 (m, 3H), 7.53 (s, 1H), 7.55-7.57 (m, 3H), 7.77 (t, J=7.63 Hz, 1H), 8.01 (d, J=7.93 Hz, 1H), 8.46 (d, J=7.93 Hz, 1H). $^{13}$C NMR (CDCl$_3$, 100 MHz) δ 37.24, 83.49, 92.93, 101.14, 123.06, 124.94, 125.37, 127.49, 127.78, 128.33, 128.44, 131.39, 132.51, 136.09, 136.61, 161.80. FTIR (cm$^{-1}$): 3065, 2926, 2858, 2249, 2214, 1652, 1615, 1488, 1444, 1316, 1247, 1179. HRMS: Calculated for C$_{18}$H$_{14}$NO [M+H]$^+$: 260.1070, found: 260.1070.

G. Synthesis of 2-methyl-5-nitroisoquinolin-1(2H)-one (O2-12) Via Procedure C Obtained as yellow solid (41 mg, 67% yield). R$_f$ (Ethyl acetate/Pet. ether=50:50)=0.5; MP=112.0° C. $^1$H NMR (400 MHz, CDCl$_3$) δ 3.65 (s, 3H), 7.29 (d, J=2.29 Hz, 2H), 7.57 (t, J=8.01 Hz, 1H), 8.41 (dd, J=7.78, 1.37 Hz, 1H), 8.76 (dd, J=8.24 Hz, 1.45 Hz, 1H). $^{13}$C NMR (CDCl$_3$, 100 MHz) δ 37.20, 100.47, 125.67, 127.92, 129.27, 130.91, 134.20, 136.05, 144.54, 161.00. FTIR (cm$^{-1}$): 2925, 2860, 1655, 1477, 1336. HRMS: Calculated for C$_{10}$H$_9$N$_2$O$_3$ [M+H]$^+$: 205.0611, found: 205.0608.

H. Synthesis of 2,6-dimethylisoquinolin-1(2H)-one (O2-13) Via Procedure C

Obtained as a white solid (33 mg, 64% yield). R$_f$ (Ethyl acetate/Pet. ether=50:50)=0.5; MP=85.6° C. $^1$H NMR (500 MHz, CDCl$_3$) δ 2.47 (s, 3H), 3.59 (s, 3H), 6.42 (d, J=7.25 Hz, 1H), 7.04 (d, J=7.25 Hz, 1H), 7.29 (d, J=7.65 Hz, 2H), 8.31 (d, J=8.77 Hz, 2H). $^{13}$C NMR (CDCl$_3$, 125 MHz) δ 21.76, 36.94, 105.82, 123.94, 125.60, 127.61, 128.46, 132.47, 137.31, 142.52, 162.63. FTIR (cm$^1$): 2926, 2826, 1645, 1712, 1606, 1466, 1382, 1351, 1300. HRMS: Calculated for C$_{11}$H$_{12}$NO [M+H]$^+$: 174.0913, found: 174.0913.

I. 2-(1-phenylethyl)isoquinolin-1(2H)-one (A2-15) Via Procedure D

35% yield at 45% conversion. % ee of product=70%; s factor 12.3

J. 6-methyl-2-(1-phenylethyl)isoquinolin-1(2H)-one (O2-16) Via Procedure D

The titled compound was prepared by following the general procedure D. Obtained as a colorless sticky liquid (3 mg, 25% yield at 40% conversion). R$_f$ (Ethyl acetate/Pet. ether=20:80)=0.55; $^1$H NMR (500 MHz, CDCl$_3$) δ 1.75 (d, J=6.87 Hz, 3H) 2.47 (s, 3H) 6.38 (d, J=7.63 Hz, 1H) 6.56 (q, J=6.99 Hz, 1H) 6.88 (d, J=7.63 Hz, 1H) 7.26 (s, 1H) 7.27-7.33 (m, 2H) 7.33-7.36 (m, 4H) 8.37 (d, J=8.01 Hz, 1H). $^{13}$C NMR (125 MHz, CDCl$_3$) δ 18.77, 21.76, 51.93, 106.35, 123.88, 125.55, 127.40, 127.73, 128.07, 128.18, 128.46, 128.73, 136.75, 140.76, 142.75, 162.03. FTIR (cm$^{-1}$): 3156, 2978, 2927, 2865, 2255, 1803, 1642, 1600, 1382, 1171, 908. HRMS: Calculated for C$_{18}$H$_{17}$ON [M+Na]$^+$: 286.1202, found: 286.1202. % ee of product=64%, s factor 9.6.

K. Synthesis of 1-Benzylquinolin-2(1H)-one (O3-1) Via Procedure B with KOH Base Crude product purified by flash silica gel column and product obtained as light red solid O3-1(51 mg, 72%). R f=0.2 in 20% EtOAc/pet ether. Melting point: 69-70° C.

$^1$H NMR (400 MHz, CDCl$_3$) δ ppm 7.76 (d, J=8.4 Hz, 1H), 7.57 (d, J=6.4 Hz, 1H), 7.42 (d, J=6.0 Hz, 1H), 7.27-7.22 (m, 7H), 6.82 (d, J=8.8 Hz, 1H), 5.57 (s, 2H); $^{13}$C NMR (400 MHz, CDCl$_3$) δ ppm 162.57, 139.69, 139.36, 136.26, 130.67, 128.85, 128.78, 127.26, 126.55, 122.27, 121.52, 120.92, 115.05, 45.90; IR: 3060, 1651, 1598 cm$^{-1}$; HRMS: calcd. for [M+H]$^+$ C$_{16}$H$_{14}$NO: 236.1075, found: 236.1070.

L. Synthesis of 1-Methylquinolin-2(1H)-one (O3-2) Via Procedure B with KOH Base Melting point: 72-75° C.

$^1$H NMR (400 MHz, CDCl$_3$) δ ppm 7.67 (d, J=9.4 Hz, 1H), 7.61-7.53 (m, 2H), 7.36 (dd, J=8.3, 0.9 Hz, 1H), 7.29-7.18 (m, 1H), 6.71 (d, J=9.5 Hz, 1H), 3.72 (s, 3H); $^{13}$C NMR (400 MHz, CDCl$_3$) δ ppm 162.52, 140.22, 139.15, 130.83, 128.94, 122.29, 121.92, 120.86, 114.34, 29.60; HRMS: calcd. for [M+H]$^+$ C$_{10}$H$_{10}$NO: 160.0762, found: 160.0757.

M. Synthesis of 10-methylacridin-9(10H)-one (O3-3) Via Procedure B with ᵗBuOK Base product obtained as solid O3-3 (40 mg, 95%). R f=0.1 in 20% EtOAc/pet ether.

$^1$H NMR (400 MHz CDCl$_3$) δ ppm 3.88 (s, 3H), 7.28 (t, J=7.2 Hz, 2H), 7.50 (d, J=8.7 Hz, 2H), 7.69-7.73 (m, 2H), 8.55 (dd, J=8.0, 1.2 Hz, 2H); $^{13}$C NMR (400 MHz CDCl$_3$) δ ppm 33.9, 115.0, 121.5, 122.7, 128.0, 134.0, 142.8, 178.3; IR (CDCl$_3$) 2917, 2850, 1637 cm$^{-1}$; HRMS: calcd. for [M+H]$^+$ C$_{14}$H$_{12}$NO: 210.0918, found: 210.0913.

N. Synthesis of 5,8-dibromo-1-methylquinolin-2 (1H)-one (O3-14) and (O4-14) Via Procedure B with ᵗBuOK Base product obtained as solid O3-14 (30 mg, 32%) with another liquid isomer O4-14 (18 mg, 20%). R f=0.5 in 40% EtOAc/pet ether.

O3-14 $^1$H NMR (200 MHz, CDCl$_3$) δ ppm 3.94 (s, 3H), 6.79 (d, J=9.73 Hz, 1H), 7.33 (d, J=8.46 Hz, 1H), 7.64 (d, J=8.46 Hz, 1H), 8.11 (d, J=9.73 Hz, 1H); HRMS: calcd. for [M+H]$^+$ C$_{10}$H$_8$Br$_2$NO: 315.8973, found: 315.8967.

O4-14: Yield 20% (+32% of 2-oxo isomer). R f=0.3 in 40% EtOAc/pet ether; $^1$H NMR (200 MHz, CDCl$_3$) δ ppm 3.74 (s, 3H), 6.80 (d, J=9.85 Hz, 1H), 7.37 (d, J=2.65 Hz, 1H), 7.44-7.55 (m, 1H), 8.14 (d, J=9.85 Hz, 1H); HRMS: calcd. for [M+H]$^+$ C$_{10}$H$_8$Br$_2$NO: 315.8973, found: 315.8975.

O. Synthesis of 3,4-dihydro-2-benzylisoquinolin-1(2H)-one (O1-1)

3,4-dihydro-2-benzylisoquinolin-2-ium tetrafluoroborate A1-1 (59 mg, 0.2 mmol) was taken in a round bottom flask with THF (3 ml) as a solvent under moisture free atmosphere. The reaction mixture was cooled to 0° C. with O$_2$ purging, then dimethyl phosphite (28 µL, 1.5 eq) and potassium carbonate (83 mg, 3 eq) was added and stirred for 3 h. After that, LiHMDS (1M in hexane, 0.7 mL, 3.5 eq) was added drop-wise at 0° C. for 2 h and the reaction was monitored by TLC. After completion, the reaction mixture was quenched with saturated ammonium chloride solution and product was extracted by ethyl acetate. The organic layer dried over Na$_2$SO$_4$ and solvent was removed in rotary evaporator. Crude product purified by flash silica gel column which gives O1-1 (17 mg, 36% yield) as solid. R f=0.2-0.25 in 20% EtOAc/pet ether.

$^1$H NMR (200 MHz, CDCl$_3$): δ ppm 2.94 (t, J=6.57 Hz, 2H) 3.5 (t, 2H) 4.80 (s, 2H) 7.16 (dt, J=6.41, 0.84 Hz, 1H) 7.20-7.49 (m, 7H) 8.15 (dd, J=7.33, 1.64 Hz, 1H).

P. Synthesis of (S)-2-(1-phenylethyl)isoquinolin-1 (2H)-one (O2-16) Via Procedure D 77% starting with chiral A and 20 mol % diphenylphosphite (DMHP) catalyst, K$_2$CO$_3$ base. 70% ee with racemic A and 20 mol % P4 cat with DABCO base at ~50% conversion

Q. Synthesis of 6-methyl-2-(1-phenylethyl)isoquinolin-1(2H)-one (O2-17) Via Procedure D 80% starting with chiral A and 20 mol % diphenylphosphite (DMHP) catalyst, K$_2$CO$_3$ base. 66% ee with racemic A and 20 mol % P4 cat with DABCO base at ~50% conversion $^1$H NMR (500 MHz, CDCl$_3$) δ 1.75 (d, J=6.87 Hz, 3H) 2.47 (s, 3H) 6.38 (d, J=7.63 Hz, 1H) 6.56 (q, J=6.99 Hz, 1H) 6.88 (d, J=7.63 Hz, 1H) 7.26 (s, 1H) 7.27-7.33 (m, 2H) 7.33-7.36 (m, 4H) 8.37 (d, J=8.01 Hz, 1H). $^{13}$C NMR (125 MHz, CDCl$_3$) δ 18.77, 21.76, 51.93, 106.35, 123.88, 125.55, 127.40, 127.73, 128.07, 128.18, 128.46, 128.73, 136.75, 140.76, 142.75, 162.03. FTIR (cm$^{-1}$): 3156, 2978, 2927, 2865, 2255, 1803, 1642, 1600, 1382, 1171, 908. HRMS: Calculated for C$_{18}$H$_{17}$ON [M+Na]$^+$: 286.1202, found: 286.1202.

Example 6: New Phosphite Catalyst (1R,7R)-9,9-dimethyl-4-hydrido-4-oxo-2,2,6,6-tetramethyl-3,5,8,10 tetraoxa-4-phosphabicyclo[5.3.0] decane (P2)

The titled compound was prepared by following the literature procedure, using 600 mg (2.75 mmol) of (4R,5R)-2,2-dimethyl-tetramethyl-TADDOL in 10 ml THF, which afforded 712 mg (98%) of the product as white crystals. R$_f$ (Ethyl acetate/Pet. ether=50:50)=0.6. MP=91.3° C. $^1$H NMR (500 MHz, CDCl$_3$) δ 1.40-1.43 (m, 9H), 1.47 (s, 3H), 1.62 (s, 3H), 1.65 (s, 3H), 3.98 (d, J=9.54 Hz, 1H), 4.47 (d, J=8.17 Hz, 1H), 6.73 (d, JH-P=732 Hz, 1H). $^{13}$C NMR (125 MHz, CDCl$_3$) δ 21.96, 21.99, 22.04, 27.00, 27.04, 28.97, 28.99, 29.66, 29.73, 80.37, 80.38, 81.65, 82.04, 82.12, 82.19, 110.40. $^{31}$P NMR (200 MHz, CDCl$_3$): δ 1.15. FTIR (cm$^{-1}$): 2979, 1597, 1445, 1371, 1243, 1164, 1076, 929, 847, 745. HRMS: Calculated for C$_{22}$H$_{42}$O$_{10}$NaP$_2$ [M]$^+$: 551.2145, found: 551.2139.

Advantages of the Invention

1. Transition metal free approach
2. Environment friendly process
3. Catalyst control regioselective oxidation
4. To achieve kinetic resolution with amines having a chiral center

The invention claimed is:

1. A single pot process for preparation of an oxo compound, wherein said process comprises:
subjecting an iminium salt to aerobic oxidation by using an in situ generated alpha radical intermediate of formula (I) or (II) in the presence of a catalytic amount of a nucleophile and a suitable base at a temperature in a range of 0 to 30° C. to afford said oxo compound,
wherein, the iminium salt comprises: (i) (E)-N,1-diphenylmethaniminum, (ii) (E)-1-(2-chloro-6-fluorophenyl)-N-phenylmethaniminium, or (iii) a bicyclic or tricyclic heteroaromatic moiety,
wherein, said in situ generated alpha radical intermediate of formula (I) or (II) is represented as,

Formula (I)

and/or

Formula (II)

wherein,
each of $R^1$, $R^2$ is selected from an alkyl or aryl,
each of $R^3$, $R^4$ and $R^5$ is selected from H, an alkyl, an aryl, an alkene, an alkoxy, an amine, an alkynyl, a halide, CO, COOH, and $NO_2$;
CAT is derived from the nucleophile selected from 1,8-Diazabicyclo(5.4.0)undec-7-ene (DBU), 1,5,7-Triazabicyclo[4.4.0]dec-5-ene (TBD), a diR-phosphite, and thiophenol, wherein, each of R is selected from H, an alkyl, an aryl, and an alkene, and wherein R may be covalently linked to each other; and
each or any combination of $R^1$, $R^2$, $R^3$, $R^4$ and $R^5$ may optionally form a cyclic ring.

2. The process as claimed in claim 1, wherein said process is a regio- and stereoselective aerobic oxidation or an oxidative kinetic resolution.

3. The process as claimed in claim 1, wherein,
the iminium salt is obtained by alkylation of an imine to form an iminium salt A, wherein the imine is optionally obtained by reacting an aldehyde with an amine in a suitable solvent;
the nucleophile or catalyst is bound to the iminium salt A in the presence of the suitable base to form a neutral compound B;
a radical compound is derived from the neutral compound B under household light;
the radical compound is transformed into the in situ generated alpha radical intermediate of formula (I) or (II); and
the in situ generated alpha radical intermediate is converted into the oxo compound.

4. The process as claimed in claim 3, wherein said imine is selected from group consisting of (E)-N,1-diphenylmethanimine or (E)-1-(2-chloro-6-fluorophenyl)-N-phenylmethanimine; said alkyl halide/triflate is selected from methyl triflate, methyl iodide, ethyl bromide, allyl bromide, and benzyl bromide; said aldehyde is selected from group consisting of benzaldehyde and 2-chloro-6-fluoro-benzaldehyde; said base is selected from group consisting of 1,8-Diazabicyclo(5.4.0)undec-7-ene, potassium carbonate, Potassium hydroxide, Potassium tert-butoxide, Lithium bis(trimethylsilyl)amide, lithium diisopropymamide, n-Butyllithium, or a combination thereof.

5. The process as claimed in claim 3, wherein said nucleophile or catalyst is selected from group consisting of 1,8-Diazabicyclo(5.4.0)undec-7-ene, 1,5,7-Triazabicyclo[4.4.0]dec-5-ene, dimethyl phosphite, (1R,7R)-9,9-dimethyl-4-hydrido-4-oxo-2,2,6,6-tetramethyl-3,5,8,10 tetraoxa-4-phosphabicyclo[5.3.0]decane, (1R,7R)-9,9-dimethyl-4-hydrido-4-oxo-2,2,6,6-tetraphenyl-3,5,8,10 tetraoxa-4-phosphabicyclo[5.3.0]decane, (1R,7R)-9,9-dimethyl-4-hydrido-4-oxo-2,2,6,6-tetra(2-methylphenyl)-3,5,8,10-tetraoxa-4-phosphabicyclo[5.3.0]decane, (1R,7R)-9,9-dimethyl-4-hydrido-4-oxo-2,2,6,6-tetra(3,5-dimethylphenyl)-3,5,8,10 tetraoxa-4-phosphabicyclo[5.3.0]decane, (1R,7R)-9,9-dimethyl-4-hydrido-4-oxo-2,2,6,6-tetranapthyl-3,5,8,10 tetraoxa-4-phosphabicyclo[5.3.0]decane, diphenyl phosphite, and thiophenol.

6. The process as claimed in claim 3, wherein said solvent is selected from group consisting of tetrahydrofuran, methyl tert-butyl ether, acetonitrile, dichloromethane, chloroform, dimethylformamide, or a mixture thereof.

7. The process as claimed in claim 3, wherein said compound A is selected from group consisting of 2-benzyl-3,4-dihydroisoquinolin-2-ium tetrafluoroborate (A1-1), 2-(o-tolyl)-3,4-dihydroisoquinolin-2-ium tetrafluoroborate (A1-3), 2-(2-methoxyphenyl)-3,4-dihydroisoquinolin-2-ium tetrafluoroborate (A1-4), 2-(naphthalen-1-yl)-3,4-dihydroisoquinolin-2-ium tetrafluoroborate (A1-5), 2-Benzylisoquinolin-2-ium tetrafluoroborate (A2-1), 2-methylisoquinolin-2-ium tetrafluoroborate (A2-2), 2-allylisoquinolin-2-ium tetrafluoroborate (A2-3), 2-benzyl-5-nitroisoquinolin-2-ium tetrafluoroborate (A2-4), 2-benzyl-3-bromoisoquinolin-2-ium tetrafluoroborate (A2-5), 3-Bromo-2-methylisoquinolin-2-ium trifluoromethanesulfonate (A2-6), 2-Methy-3-phenylisoquinolin-2-ium trifluoromethanesulfonate (A2-7), 4-Bromo-2-methylisoquinolin-2-ium trifluoromethanesulfonate (A2-8), 2-Methyl-4-(phenylethynyl)isoquinolin-2-ium trifluoromethanesulfonate (A2-9), 5-Methylphenanthridin-5-ium trifluoromethanesulfonate (A2-10), 2-Methylphthalazin-2-ium trifluoromethanesulfonate (A2-11), 2-Methyl-5-nitroisoquinolin-2-ium trifluoromethanesulfonate (A2-12), 2,6-Dimethylisoquinolin-2-ium trifluoromethanesulfonate (A2-13), 5,8-dibromo-2-methylisoquinolin-2-ium trifluoromethanesulfonate (A2-14), 2-(1-phenylethyl)isoquinolin-2-ium trifluoromethanesulfonate (A2-15), 6-methyl-2-(1-phenylethyl)isoquinolin-2-ium trifluoromethanesulfonate (A2-16), 1-benzylquinolin-1-ium tetrafluoroborate (A3-1), 1-methylquinolin-1-ium tetrafluoroborate (A3-2), 1-ethylquinolin-1-ium tetrafluoroborate (A3-3), 1-methyl-3-phenylquinolin-1-ium trifluoromethanesulfonate (A3-4), 3-bromo-1-methylquinolin-1-ium trifluoromethanesulfonate (A3-5), 3-(dimethylamino)-1-methylquinolin-1-ium trifluoromethanesulfonate (A3-6), 1,4-dimethylquinolin-1-ium trifluoromethanesulfonate (A3-7), 4-methoxy-1-methylquinolin-1-ium trifluoromethanesulfonate (A3-8), 1-methyl-5-nitroquinolin-1-ium trifluoromethanesulfonate (A3-9), 8-hydroxy-1-methylquinolin-1-ium trifluoromethanesulfonate (A3-10), 8-methoxy-1-methylquinolin-1-ium trifluoromethanesulfonate (A3-11), 8-(allyloxy)-1-methylquinolin-1-ium trifluoromethanesulfonate (A3-12), 1-methyl-8-nitroquinolin-1-ium trifluoromethanesulfonate (A3-13), 5,8-dibromo-1-methylquinolin-1-ium trifluoromethanesulfonate (A3-14), 8-bromo-1-methylquinolin-1-ium trifluoromethanesulfonate (A3-15), 2-(methoxycarbonyl)-1-methylquinolin-1-ium trifluoromethanesulfonate (A3-16), and 10-methylacridin-10-ium trifluoromethanesulfonate (A3-17).

8. The process as claimed in claim 3, wherein said compound B is selected from group consisting of Dimethyl (2-benzyl-1,2,3,4-tetrahydroisoquinolin-1-yl)phosphonate (B1-1), Dimethyl (2-(o-tolyl)-1,2,3,4-tetrahydroisoquinolin-1-yl)phosphonate (B1-3), Dimethyl (2-(2-methoxyphenyl)-1,2,3,4-tetrahydroisoquinolin-1-yl)phosphonate (B1-4), Dimethyl (2-(2-methoxyphenyl)-1,2,3,4-tetrahydroisoquinolin-1-yl)phosphonate (B1-4), Dimethyl (2-benzyl-1,2-dihydroisoquinolin-1-yl)phosphonate (B2-1), Dimethyl (2-methyl-1,2-dihydroisoquinolin-1-yl)phosphonate (B2-2), Dimethyl (2-allyl-1,2-dihydroisoquinolin-1-yl)phosphonate (B2-3), Dimethyl (2-benzyl-5-nitro-1,2-dihydroisoquinolin-1-yl)phosphonate (B2-4), Dimethyl (2-benzyl-3-bromo-1,2- dihydroisoquinolin-1-yl)phosphonate (B2-5), Dimethyl (3-bromo-2-methyl-1,2-dihydroisoquinolin-1-yl)phosphonate (B2-6), Dimethyl (2-methyl-3-phenyl-1,2-dihydroisoquinolin-1-yl)phosphonate(B2-7), Dimethyl (4-bromo-2-methyl-1,2-dihydroisoquinolin-1-yl)phosphonate (B2-8), Dimethyl (2-methyl-4-(phenylethynyl)-1,2-dihydroisoquinolin-1-yl)phosphonate (B2-9), Dimethyl (5-methyl-5,6-dihydrophenanthridin-6-yl)phosphonate (B2-10), Dimethyl (2-methyl-1,2-dihydrophthalazin-1-yl)phosphonate (B2-11), Dimethyl (2-methyl-5-nitro-1,2-dihydroisoquinolin-1-yl)phosphonate (B2-12), Dimethyl (2,6-dimethyl-1,2-dihydroisoquinolin-1-yl)phosphonate (B2-13), Dimethyl (5,8-dibromo-2-methyl-1,2-dihydroisoquinolin-1-yl) phosphonate (B2-14), Dimethyl (2-(1-phenylethyl)-1,2-dihydroisoquinolin-1-yl)phosphonate (B2-15), Dimethyl (6-methyl-2-(1-phenylethyl)-1,2-dihydroisoquinolin-1-yl) phosphonate (B2-16), 2,2-dimethyl-4,4,8,8-tetra(naphthalen-1-yl)-6-(2-(1-phenylethyl)-1,2-dihydroisoquinolin-1-yl)tetrahydro-[1,3]dioxolo[4,5-e][1,3,2]dioxaphosphepine 6-oxide (B2-17), 2,2-dimethyl-6-(6-methyl-2-(1-phenylethyl)-1,2-dihydroisoquinolin-1-yl)-4,4,8,8-tetra(naphthalen-1-yl)tetrahydro-[1,3]dioxolo[4,5-e][1,3,2]dioxaphosphepine 6-oxide (B2-18), -(4-bromo-2-methyl-1,2-dihydroisoquinolin-1-yl)-2,2,4,4,8,8-hexamethyltetrahydro-[1,3]dioxolo[4,5-e][1,3,2]dioxaphosphepine 6-oxide (B2-19), 2-Benzyl-1-(phenylthio)-1,2-dihydroisoquinoline (B2-20), Diphenyl (2-benzyl-1,2-dihydroisoquinolin-1-yl) phosphonate (B2-26), 1-(2-benzyl-1,2-dihydroisoquinolin-1-yl)-2,3,4,6,7,8,9,10-octahydropyrimido[1,2-a]azepin-1-ium (B2-21), 1-(2-benzyl-1,2-dihydroisoquinolin-1-yl)-3,4,6,7,8,9-hexahydro-2H-pyrimido[1,2-a]pyrimidin-1-ium (B2-22), 1-(2-methyl-1,2-dihydroisoquinolin-1-yl)-3,4,6,7,8,9-hexahydro-2H-pyrimido[1,2-a]pyrimidin-1-ium (B2-23), 1-(2-methyl-1,2-dihydroisoquinolin-1-yl)-2,3,4,6,7,8,9,10-octahydropyrimido[1,2-a]azepin-1-ium (B2-24), 2-methyl-1-(phenylthio)-1,2-dihydroisoquinoline (B-25), Dimethyl (1-benzyl-1,2-dihydroquinolin-2-yl)phosphonate (B3-1), Dimethyl (1-methyl-1,2-dihydroquinolin-2-yl)phosphonate (B3-2), Dimethyl (1-ethyl-1,2-dihydroquinolin-2-yl)phosphonate (B3-3), Dimethyl (1-methyl-3-phenyl-1,2-dihydroquinolin-2-yl)phosphonate (B3-4), 1-(3-bromo-1-methyl-1,2-dihydroquinolin-2-yl)-2,3,4,6,7,8,9,10-octahydropyrimido[1,2-a]azepin-1-ium (B3-5), Dimethyl (3-(dimethylamino)-1-methyl-1,2-dihydroquinolin-2-yl) phosphonate (B3-6), Dimethyl (1,4-dimethyl-1,2-dihydroquinolin-2-yl)phosphonate (B3-7), Dimethyl (4-methoxy-1-methyl-1,2-dihydroquinolin-2-yl)phosphonate (B3-8), Dimethyl (1-methyl-5-nitro-1,2-dihydroquinolin-2-yl)phosphonate (B3-9), Dimethyl (8-hydroxy-1-methyl-1,2-dihydroquinolin-2-yl)phosphonate (B3-10), Dimethyl (8-methoxy-1-methyl-1,2-dihydroquinolin-2-yl)phosphonate (B3-11), Dimethyl (8-(allyloxy)-1-methyl-1,2-dihydroquinolin-2-yl)phosphonate (B3-12), Dimethyl (1-methyl-8-nitro-1,2-dihydroquinolin-2-yl)phosphonate (B3-13), Dimethyl (5,8-dibromo-1-methyl-1,2-dihydroquinolin-2-yl) phosphonate (B3-14), Dimethyl (5,8-dibromo-1-methyl-1,4-dihydroquinolin-4-yl)phosphonate (B3-18), Dimethyl (8-bromo-1-methyl-1,2-dihydroquinolin-2-yl)phosphonate (B3-15), Dimethyl (8-bromo-1-methyl-1,4-dihydroquinolin-4-yl)phosphonate (B3-19), Methyl 4-(dimethoxyphosphoryl)-1-methyl-1,4-dihydroquinoline-2-carboxylate (B3-16), Dimethyl (10-methyl-9,10-dihydroacridin-9-yl) phosphonate (B3-17), and dimethyl ((methyl(phenyl)amino)(phenyl)methyl)phosphonate (B5).

9. The process as claimed in claim 1, wherein said oxo compound is selected from group consisting of 3,4-dihydro-2-benzylisoquinolin-1(2H)-one (O1-1), 2-(o-tolyl)-3,4-dihydroisoquinolin-1(2H)-one (O1-3), 2-(2-methoxyphenyl)-3,4-dihydroisoquinolin-1(2H)-one (O1-4), 2-(naphthalen-1-yl)-3,4-dihydroisoquinolin-1(2H)-one (O1-5), 2-benzylisoquinolin-1(2H)-one (O2-1), 2-methylisoquinolin-1(2H)-one (O2-2), 2-benzyl-5-nitroisoquinolin-1(2H)-one (O2-3), 2-benzyl-3-bromoisoquinolin-1(2H)-one (O2-4), 2-allylisoquinolin-1(2H)-one (O2-5), 3-bromo-2-methylisoquinolin-1(2H)-one (O2-7), 2-methyl-3-phenylisoquinolin-1(2H)-one (O2-8), 4-bromo-2-methylisoquinolin-1(2H)-one (O2-9), 2-methyl-4-(phenylethynyl)isoquinolin-1(2H)-one (O2-10), 5-methylphenanthridin-6(5H)-one (O2-11), 2-methylphthalazin-1(2H)-one (O2-12), 2-methyl-5-nitroisoquinolin-1(2H)-one (O2-13), 2,6-dimethylisoquinolin-1(2H)-one (O2-14), 5,8-dibromo-2-methylisoquinolin-1(2H)-one (O2-15), (S)-2-(1-phenylethyl)isoquinolin-1(2H)-one (O2-16), 1-benzylquinolin-2(1H)-one (O3-1), 1-methylquinolin-2(1H)-one (O3-2), 1-ethylquinolin-2(1H)-one (O3-3), 1-methyl-3-phenylquinolin-2(1H)-one (O3-4), 3-bromo-1-methylquinolin-2(1H)-one (O3-5), 3-(dimethylamino)-1-methylquinolin-2(1H)-one (O3-6), 1,4-dimethylquinolin-2(1H)-one (O3-7), 4-methoxy-1-methylquinolin-2(1H)-one (O3-8), 1-methyl-5-nitroquinolin-2(1H)-one (O3-9), 8-hydroxy-1-methylquinolin-2(1H)-one (O3-10), 8-methoxy-1-methylquinolin-2(1H)-one (O3-11), 8-(allyloxy)-1-methylquinolin-2(1H)-one (O3-12), 1-methyl-8-nitroquinolin-2(1H)-one (O3-13), 5,8-dibromo-1-methylquinolin-2(1H)-one (O3-14), 8-bromo-1-methylquinolin-2(1H)-one (O3-15), 5,8-dibromo-1-methylquinolin-4(1H)-one (O4-14), 8-bromo-1-methylquinolin-4(1H)-one (O4-15), methyl 1-methyl-4-oxo-1,4-dihydroquinoline-2-carboxylate (O4-1), and 10-methylacridin-9(10H)-one (O4-2).

* * * * *